United States Patent [19]

Katagiri et al.

[11] Patent Number: 4,816,178

[45] Date of Patent: Mar. 28, 1989

[54] OPTICALLY ACTIVE COMPOUND AND LIQUID CRYSTAL COMPOSITION CONTAINING SAME

[75] Inventors: Kazuharu Katagiri, Tama; Kenji Shinjo, Yokohama; Kazuo Yoshinaga, Machida, all of Japan

[73] Assignee: Canon Kabushiki Kaisha, Tokyo, Japan

[21] Appl. No.: 42,814

[22] Filed: Apr. 27, 1987

[30] Foreign Application Priority Data

Apr. 30, 1986 [JP] Japan .................................. 61-97853
Apr. 30, 1986 [JP] Japan .................................. 61-97854

[51] Int. Cl.$^4$ .................... C09K 19/52; C09K 19/06; C09K 19/12; C07C 152/07
[52] U.S. Cl. ........................... 252/299.6; 252/299.01; 252/299.5; 252/299.65; 252/299.66; 350/350 R; 350/350 S; 558/252; 558/257; 568/23; 568/25; 568/67
[58] Field of Search ........... 252/299.6, 299.65, 299.01, 252/299.5, 299.66, 299.67; 350/350 R, 350 S; 558/252, 257

[56] References Cited

U.S. PATENT DOCUMENTS

| | | | |
|---|---|---|---|
| 4,137,250 | 1/1979 | Reynolds et al. | 252/299.67 |
| 4,162,988 | 7/1979 | Maze et al. | 252/299.65 |
| 4,427,569 | 1/1984 | Margerum et al. | 252/299.65 |
| 4,596,667 | 6/1986 | Inukai et al. | 252/299.65 |
| 4,613,209 | 9/1986 | Goodby et al. | 252/299.65 |
| 4,615,586 | 10/1986 | Geary et al. | 252/299.65 |
| 4,653,866 | 3/1987 | Era et al. | 252/299.65 |

FOREIGN PATENT DOCUMENTS

| | | | |
|---|---|---|---|
| 2603293 | 8/1977 | Fed. Rep. of Germany | 252/299.6 |
| 56-108761 | 8/1981 | Japan | 252/299.6 |
| 59-128357 | 7/1984 | Japan | 252/299.6 |

OTHER PUBLICATIONS

Demus, D. et al., Flussige Kristalle in Tabellen II, VEB Deutscher Verlag fur Grundstoffindustrie, Leipzig, pp. 138–141, (1984).
Gray, G. W. et al., Liquid Crystals & Plastic Crystals, vol. 1, Ellis Horwood, Ltd., London, pp. 142–143, (1974).
Heppke et al., "Phasen mit der Grandjean–Cano–Methods", Z. Naturforsch, 32a, pp. 899–901, (1977).
Tinh et al., Mol. Cryst. Liq. Cryst., Lett. Sect., 4, pp. 93–98, (1987).

Primary Examiner—Teddy S. Gron
Attorney, Agent, or Firm—Fitzpatrick, Cella, Harper & Scinto

[57] ABSTRACT

An optically active 4-alkylbenzenethiol and an optically active bis(4-alkylphenyl)disulfide represented by the formula:

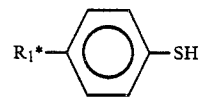

and

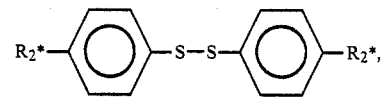

respectively, wherein $R_1^*$ and $R_2^*$ are respectively an alkyl group having 4–12 carbon atoms including an asymmetric carbon atom, may be prepared, e.g., through halogenation or sulfonation of an optically active alcohol, followed by reaction with a phenylmagnesium halide, chlorosulfonylation and reduction. The optically active thiol or disulfide is effective, e.g., in preventing occurrence of reverse domain when added to a nematic liquid crystal, and also can be bonded to an intermediate to provide a functional material including a mesomorphic compound represented by the formula:

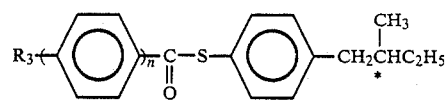

wherein $R_3$ is an alkyl or alkoxy group having 1–18 carbon atoms, n is 1 or 2, and C* is an asymmetric carbon atom.

13 Claims, No Drawings

OPTICALLY ACTIVE COMPOUND AND LIQUID CRYSTAL COMPOSITION CONTAINING SAME

FIELD OF THE INVENTION AND RELATED ART

The present invention relates to a novel optically active compound, and a liquid crystal composition containing the same. The present invention also relates to a mesomorphic compound produced from the optically active compound, a chiral liquid crystal composition containing the same, and a liquid crystal device using the liquid crystal composition.

There have been known various types of optical devices characterized by having optical activities as will be exemplified as follows:

(1) Those utilizing a cholesteric-nematic phase transition in a liquid crystal state (J. J. Wysoki, A. Adams and W. Haas: Phys. Rev. Lett., 20, 10204 (1968));

(2) Those utilizing a guest-host effect of the White-Taylor type in a liquid crystal state (D. L. White and G. N. Taylor: J. Appl. Phys., 45, 4718 (1974));

(3) Those utilizing a ferroelectric liquid crystal effect of a chiral smectic C phase, H phase, F phase, I phase or G phase (N. A. Clark and S. T. Lagerwall: Appl. Phys. Lett., 36, 899 (1980));

(4) Others including notch filters or band path filters utilizing selective scattering characteristics of a material having a cholesteric phase in the liquid crystal state when fixed in a matrix (F. J. Kahn: Appl. Phys. Lett. 18, 231 (1971)): and circular polarization beam splitters utilizing circular polarization characteristics (S. D. Jacobs, SPIE, 37, 98 (1981)).

These optical devices are important as display devices and modulation devices, while the explanation of the individual systems is left to the respective references and omitted.

Functional materials constituting these optical devices contain an optically active compound or substance as a major component thereof or as a component which is used in a relatively small proportion but constitutes a functionally important part. Many of such optically active functional compounds are synthesized through an intermediate which per se is optically active.

Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives.

However, these intermediates involve respective problems as follows. Thus, optically active chain hydrocarbon derivatives are difficult to modify their structures and very expensive except for a particular class thereof. Amino acid derivatives are relatively cheap and easy to modify their structures, whereas N-hydrogens therein are chemically active and liable to cause hydrogen bonding or other chemical reactions so that the performances of the resultant functional material can be restricted thereby. Camphor derivatives and cholesterol derivatives are difficult to modify the structures and the steric hindrance is liable to provide ill effects to the performances of hhe resultant functional materials.

The above problems have posed a serious constraint on development of various materials.

On the other hand, there have been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127-128. In this type of liquid crystal devices, the number of pixels or picture elements have been restricted, because there is a problem that a crosstalk phenomenon occurs when a device of a matrix electrode structure with a high density of pixels is driven according to a time-sharing of time-division driving scheme. Further, their uses for display have been limited because of slow electric field response and poor visual angle characteristics.

As another type of liquid crystal device, there has been known one comprising a plurality of pixels each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924). As the bistable liquid crystal, a ferroelectric crystal showing a chiral smectic C phase (SmC*) or H phase (SmH*) is generally used.

Such a ferroelectric liquid crystal has very rapid response speed on account of having spontaneous polarization, can also exhibit memorizable bistable state and further have excellent vision angle characteristic, and therefore it is suitable for a display of large capacity and large picture area. However, known ferroelectric liquid crystal compounds generally show a chiral smectic phase at a relatively high temperature, so that it is difficult to drive them at or around room temperature.

SUMMARY OF THE INVENTION

A principal object of the present invention is to provide a significant step to solution of the above described problems. More specifically, an object of the invention is to provide a compound which can be combined with an intermediate for a functional material having appropriate inter-molecular force and shape without imparing an optical activity, and therefore susceptible of arbitrary molecular designing.

Another specific object of the present invention is to provide a mesomorphic compound capable of readily changing the length of the alkyl chain and therefore capable of controlling a kind of liquid crystal phase to be developed in the liquid crystal state and a temperature range therefor as shown by H. Arnold: Z. Phys. Chem., 226,146 (1964), and a liquid crystal composition containing at least one of such mesomorphic compounds. A further object of the present invention is to provide a compound capable of easily controlling the hydrophobic group and being stably formed into a film when applied to the LB (Langmuir-Blodget) film process for preparing an accumulation of single molecular films.

A further object of the present invention is to provide a mesomorphic compound having a smectic liquid crystal phase around room temperature or having an effect of lowering and enlarging the temperature range of a chiral smectic C-phase (SmC*) when mixed as a component, a liquid crystal composition containing at least one species of such a mesomorphic compound, and a liquid crystal device using the liquid crystal composition.

The present invention provides an optically active compound, which is an optically active 4-alkylbenzenethiol represented by the formula:

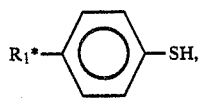

wherein $R_1^*$ is an alkyl group having 4–12 carbon atoms including an asymmetric carbon atom, and also a liquid crystal composition containing at least one species of the optically active compound.

The present invention further provides an optically active bis(4-alkylphenyl) disulfide represented by the formula:

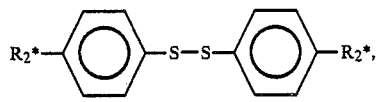

wherein $R_2^*$ is an alkyl group having 4–12 carbon atoms including an asymmetric carbon atom, and also a liquid crystal composition containing at least one species of the optically active disulfide.

As the optically active compound represents by the above formulas 1-1 and 1-2 have an asymmetric carbon atom and a thiol group or a sulfur atom by the medium of a benzene ring, they are readily provide various derivatives with a thiol carboxylic acid-ester bond, a sulfide bond, a sulfoxide bond, etc., without losing their optical activity, so that they are expected to be very extensively utilized. Up to now, however, no optically active compounds represented by the formula 1-1 or 1-2 have been known.

Based on the above knowledge, we have made an extensive study and, as a result thereof, have succeeded in synthesis of compounds represented by the formulas 1-1 and 1-2 to accomplish the present invention.

The present invention further provides a mesomorphic compound derived from the optically active compound of the formula 1-1, which mesomorphic compound is represented by the formula:

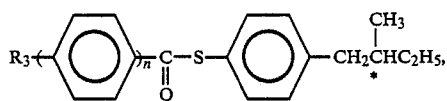

wherein $R_3$ is an alkyl or alkoxy group having 1–18 carbon atoms, n is 1 or 2, and C* is an asymmetric carbon atom.

The present invention further provides a liquid crystal composition containing at least one species of the mesomorphic compound, and also a liquid crystal device using the liquid crystal composition.

The above mentioned and other objects and features of the invention will be better understood upon consideration of the following detailed description concluding with specific examples of practice.

DETAILED DESCRIPTION OF THE INVENTION

First of all, a process for obtaining the optically active compound according to the present invention will be described.

In order to produce the optically active 4-alkyl-benzenethiol represented by the formula 1-1 according to the present invention, an optically active aliphatic alcohol may suitably be used. Specific examples thereof include: 3-methylpentanol, 4-methylhexanol, 1-methylheptanol, 2-methylbutanol, 2-methyloctanol, 2-methylnonanol, 2-methyldecanol, etc.

The optically active alcohol is halogenized or sulfonated and then readed with phenylmagnesium halide to form an optically active alkylbenzene, which is then chlorosulfonylated. The thus obtained (4-alkyl)phenylsulfonylchloride is reduced to form an optically active 4-alkylbenzenethiol of the formula 1-1 and an optically active bis(4-alkylphenyl) disulfide of the formula 1-2.

The optically active bis(4-alkylphenyl) disulfides of the formula 1-2 may be obtained by changing, e.g., the conditions for reducing the optically active 4-alkyphenylsulfonylchlorides obtained in the same manner as above. The optically active 4-alkylbenzenethiols of the formula 1-1 may also be obtained by further reducing the disulfides of the formula 1-2 thus formed.

The above mentioned synthesis processes may be summarized as follows:

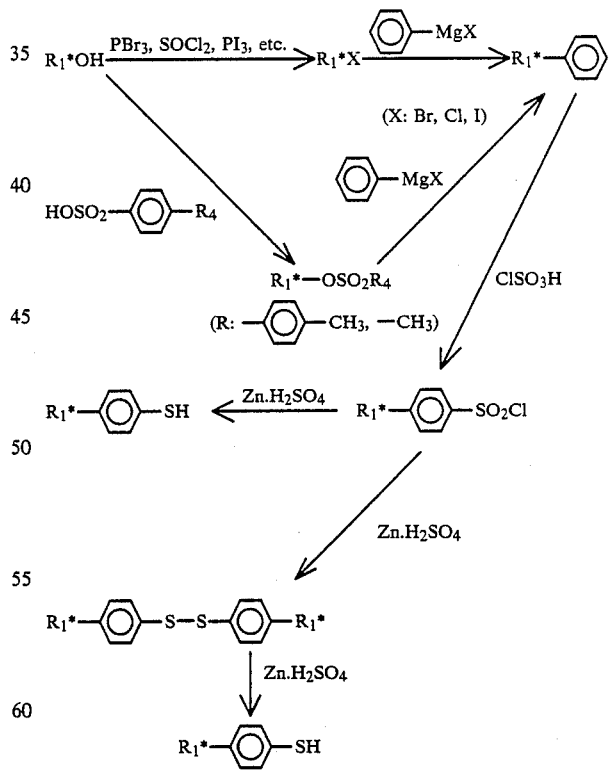

Specific examples of the thus obtained optically active compounds of the formulas 1-1 and 1-2 include the following:

(+)-4-(2'-methylbutyl)benzenethiol,
(+)-4-(1'-methylpropyl)benzenethiol, (−)-4-(1′-methylpropyl)benzenethiol,
(+)-4-(1′-methylhexyl)benzenethiol,
(−)-4-(1′-methylhexyl)benzenethiol,
(+)-4-(1′,3′-dimethylpropyl)benzenethiol,
(−)-4-(1′,3′-dimethylpropyl)benzenethiol,
(+)-4-(1′-methylbutyl)benzenethiol,
(−)-4-(1′-methylbutyl)benzenethiol,
(+)-4-(3′-methylpentyl)benzenethiol,
(−)-4-(2′-methyloctyl)benzenethiol,
(−)-4-(2′-methylnonyl)benzenethiol,
(−)-4(2′-methyldecyl)benzenethiol,
(+)-4-(4′-methylhexyl)benzenethiol,
(+)-bis(4-(2′-methylbutyl)phenyl) disulfide,
(+)-bis(4-(1′-methylpropyl)phenyl) disulfide,
(−)-bis(4-(1′-methylpropyl)phenyl) disulfide,
(+)-bis(4-(1′-methylhexyl)phenyl) disulfide,
(−)-bis(4-(1′-methylhexyl)phenyl) disulfide,
(+)-bis(4-(1′,3′-dimethylpropyl)phenyl) disulfide,
(−)-bis(4-(1′,3′-dimethylpropyl)phenyl) disulfide,
(+)-bis(4-(1′-methylbutyl)phenyl) disulfide,
(−)-bis(4-(1′-methylbutyl)phenyl) disulfide,
(+)-bis(4-(3′-methylpentyl)phenyl) disulfide, nematic liquid crystal. In this case, it is preferred to use the compound in a proportion of 0.01–50 wt. % of the liquid crystal composition.

Further, the optically active compound may be added to a nematic liquid crystal to provide a chiral smectic liquid crystal composition which may be used in a phase transition type liquid crystal device, or a White-Taylor type guest-host liquid crystal device. In this case, the compound may preferably be used in a proportion of 0.01–80 wt. % of the liquid crystal composition.

Further, the optically active compound represented by the formula 1-1, when added in a proportion of, e.g., 0.01–80 wt. % to a liquid crystal composition which per se shows a chiral smectic liquid crystal state, can improve the characteristics such as durability. Further, when added to a smectic liquid crystal as represented by the formula (1)–(5) below, it can provide a liquid crystal composition showing a ferroelectric chiral smectic phase. In this case, the compound may preferably be added in a proportion of 0.01–80 wt. % of the liquid crystal composition.

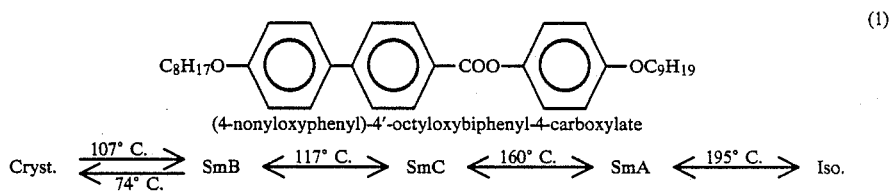

(1)

(4-nonyloxyphenyl)-4′-octyloxybiphenyl-4-carboxylate

Cryst. $\xrightarrow{107° C.}_{\xleftarrow{74° C.}}$ SmB $\xleftrightarrow{117° C.}$ SmC $\xleftrightarrow{160° C.}$ SmA $\xleftrightarrow{195° C.}$ Iso.

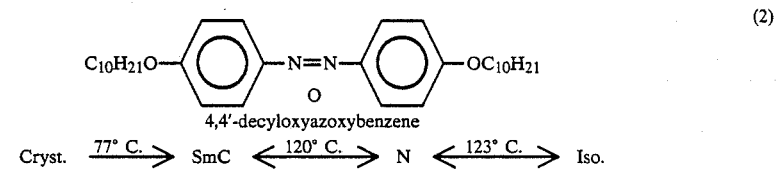

(2)

4,4′-decyloxyazoxybenzene

Cryst. $\xrightarrow{77° C.}$ SmC $\xleftrightarrow{120° C.}$ N $\xleftrightarrow{123° C.}$ Iso.

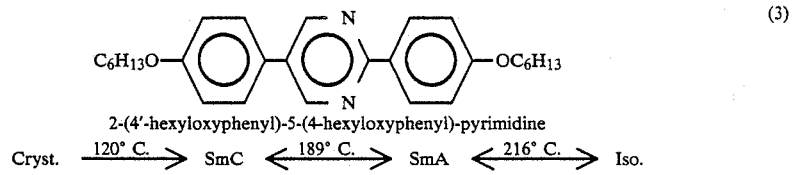

(3)

2-(4′-hexyloxyphenyl)-5-(4-hexyloxyphenyl)-pyrimidine

Cryst. $\xrightarrow{120° C.}$ SmC $\xleftrightarrow{189° C.}$ SmA $\xleftrightarrow{216° C.}$ Iso.

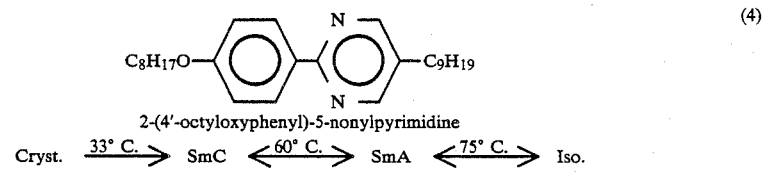

(4)

2-(4′-octyloxyphenyl)-5-nonylpyrimidine

Cryst. $\xrightarrow{33° C.}$ SmC $\xleftrightarrow{60° C.}$ SmA $\xleftrightarrow{75° C.}$ Iso.

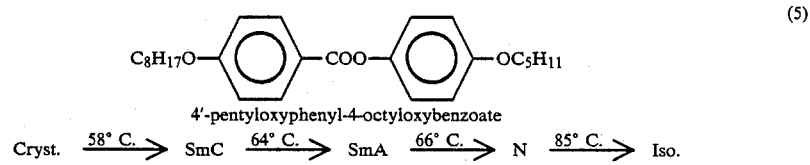

(5)

4′-pentyloxyphenyl-4-octyloxybenzoate

Cryst. $\xrightarrow{58° C.}$ SmC $\xrightarrow{64° C.}$ SmA $\xrightarrow{66° C.}$ N $\xrightarrow{85° C.}$ Iso.

(−)-bis(4-(3′-methylpentyl)phenyl) disulfide,
(−)-bis(4-(2′-methyloctyl)phenyl) disulfide,
(−)-bis(4-2′-methylnonyl)phenyl) disulfide,
(−)-bis(4-2′-methyldecyl)phenyl) disulfide.
(+)-bis(4-(4′-methylhexyl)phenyl) disulfide.

The thus obtained optically active compound represented by the formula 1-1 or 1-2 is effective in preventing occurrence of reverse domain when added to a Herein, the symbols respectively denote the following phases:
Cryst.: crystal phase
SmA: smectic A phase
SmB: smectic B phase
SmC: smectic C phase N: nematic phase
Iso.: isotropic phase As described above, the optically active compound of the formula 1-1 or 1-2 is effectively used as a material for improving the performances of a ferroelectroic liquid crystal device or a TN-type liquid crystal device.

The mesomorphic compounds of the formula 2-1 may be synthesized from an optically active intermediate such as 4-(2'-methylbutyl)benzenethiol represented by the formula 1-1. For example, the mesomorphic compounds of the formula 2-1 may be synthesized through a process represented by the following scheme from such an optically active intermediate.

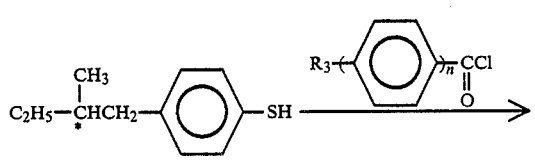

2-1

-continued

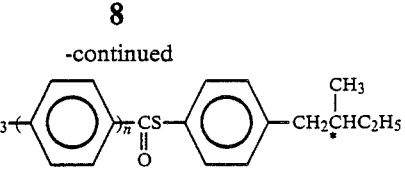

Herein, the symbols $R_3$, n and C* have the same meanings as defined above.

The mesomorphic compound represented by the formula 2-1 may be controlled with respect to the type and the temperature range of its liquid crystal phase by adjusting the number of carbon atoms in the group $R_3$. The number of carbon atoms may generally be 1–18, while the number of 4–16, particularly 6–12, is preferred from the viscosity and the temperature range of SmC* phase.

The following Table 1 shows some examples of the mesomorphic compound obtained in this manner. In the column of "phase transition temperature", the numerals represents degrees in Celsius (°C.), and the symbols other than those defined above denote the following phases.

SmC*: chiral smectic C phase, Ch.: cholesteric phase, $S_3$: a smectic phase other than SmC and SmC*.

TABLE 1

R₃─⟨◯⟩ₙ─C(=O)─S─⟨◯⟩─CH₂CH(CH₃)C₂H₅ *

| Example | $R_3$ | n | Phase Transition Temperature |
|---|---|---|---|
| 2-1 | $C_8H_{17}O-$ | 1 | Cryst. →55→ Ch ⇌68/66 Iso. ; ↖13 $S_3$ ⇌17 SmC* ↙43 |
| 2-2 | $C_{12}H_{25}O-$ | 1 | Cryst. →55→ SmC* ⇌57/54 SmA ⇌69/66 ; ↖15 $S_3$ ↙27 ; Ch ⇌70/68 Iso. |
| 2-3 | $C_7H_{15}-$ | 2 | Cryst. ⇌120/116 SmC* ⇌132/129 SmA ⇌168/165 ; Ch ⇌181/178 Iso. |
| 2-4 | $C_{13}H_{27}$ | 1 | Cryst. →39→ Iso ; ↖-1 $S_3$ ⇌23 SmA ⇌35 Ch ↙36 |
| 2-7 | $C_{10}H_{21}O-$ | 1 | Cryst. ⇌45/24 SmC* ⇌52/51 SmA ⇌59/58 ; Ch. ⇌67/66 Iso. |

TABLE 1-continued

![Structure with R3-(phenyl)n-C(=O)-S-phenyl-CH2CH(CH3)C2H5]

| Example | R3 | n | Phase Transition Temperature |
|---|---|---|---|
| 2-8 | C9H19O | 1 | Cryst. →68→ Iso; ↘33 SmC* ←50— SmA ←53— Ch ↖65 |

The liquid crystal composition according to the present invention contains at least one species of the mesomorphic compound represented by the formula 2-1. for example, the mesomorphic compound represented by the formula (I) may be mixed with a ferroelectric liquid crystal selected from those of the formulas (1)–(13) shown below to lower and enlarge the temperature range SmC*. In this case, it is preferred to use the mesomorphic compound represented by the formula 2-1 in an amount constituting 1–99 wt. %, particularly 5–95 wt. % of the resulting liquid crystal composition.

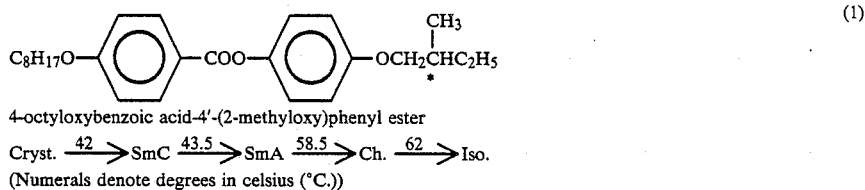

4-octyloxybenzoic acid-4'-(2-methyloxy)phenyl ester

Cryst. —42→ SmC —43.5→ SmA —58.5→ Ch. —62→ Iso.
(Numerals denote degrees in celsius (°C.))

(1)

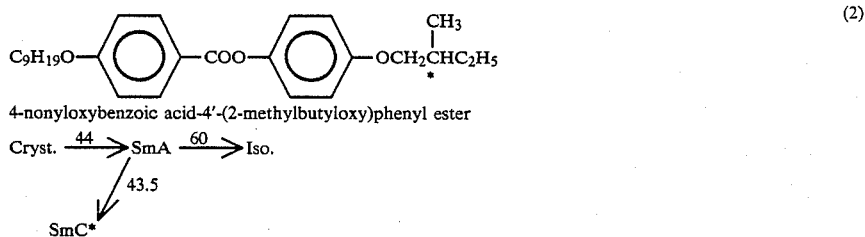

4-nonyloxybenzoic acid-4'-(2-methylbutyloxy)phenyl ester

Cryst. —44→ SmA —60→ Iso.
↘43.5
SmC*

(2)

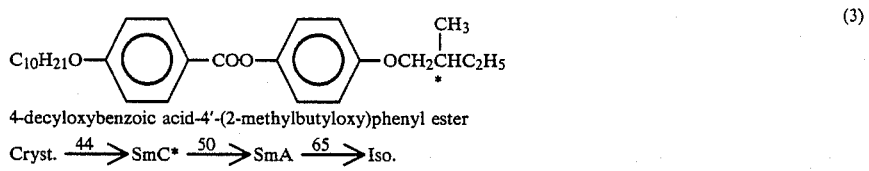

4-decyloxybenzoic acid-4'-(2-methylbutyloxy)phenyl ester

Cryst. —44→ SmC* —50→ SmA —65→ Iso.

(3)

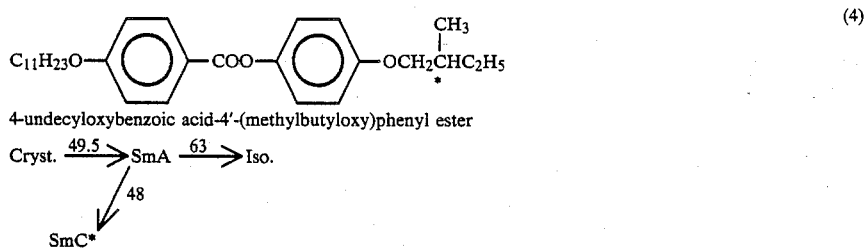

4-undecyloxybenzoic acid-4'-(methylbutyloxy)phenyl ester

Cryst. —49.5→ SmA —63→ Iso.
↘48
SmC*

(4)

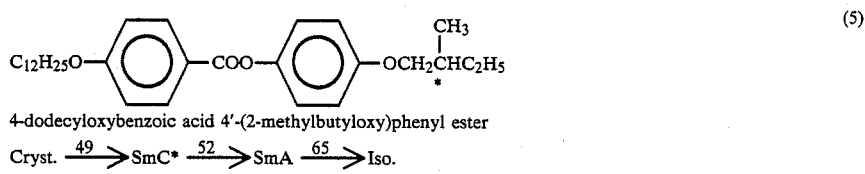

4-dodecyloxybenzoic acid 4'-(2-methylbutyloxy)phenyl ester

Cryst. —49→ SmC* —52→ SmA —65→ Iso.

(5)

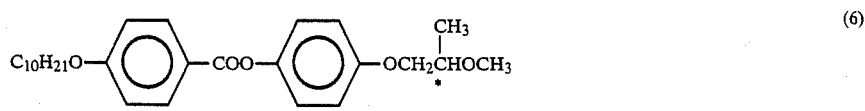

(6)

4-decyloxybenzoic acid 4'-(2-methylbutyloxy)phenyl ester

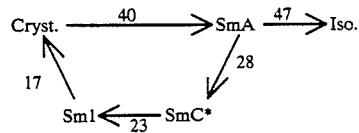

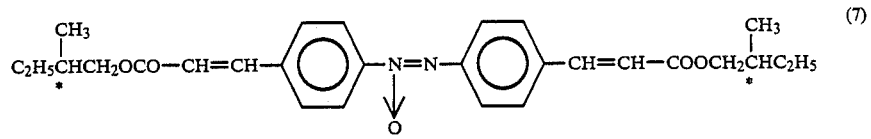

4,4'-azoxycinnamic acid bis(2-methylbutyl)ester

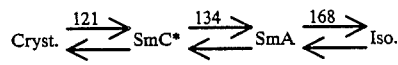

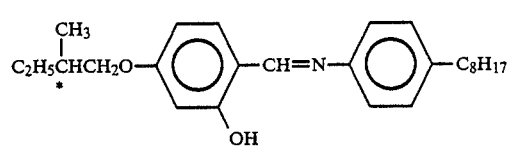

4-o-(2-methyl)butylresorcylidene-4'-octylaniline (MBRA 8)

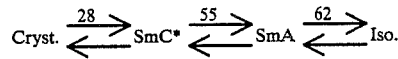

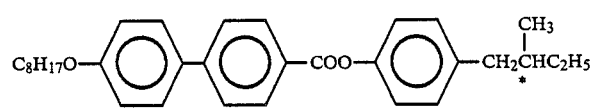

4-(2'-methylbutyl)phenyl-4'-octyloxybiphenyl-4-carboxylate

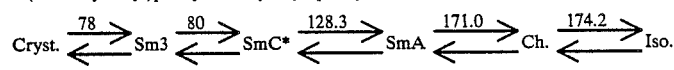

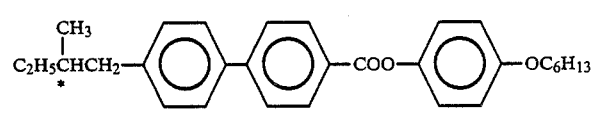

4-hexyloxyphenyl-4-(2''-methylbutyl)biphenyl-4'-carboxylate

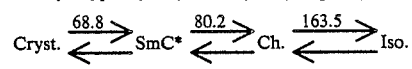

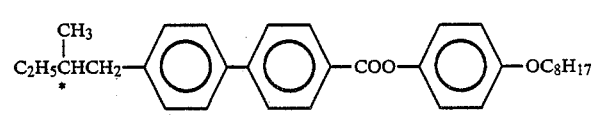

4-octyloxyphenyl-4-(2''-methylbutyl)biphenyl-4'-carboxylate

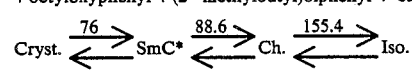

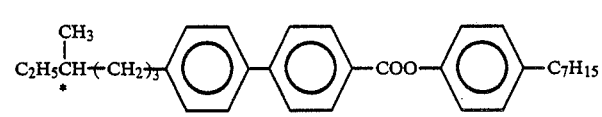

4-heptylphenyl-4-(4''-methylhexyl)biphenyl-4'-carboxylate

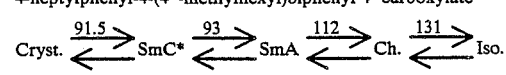

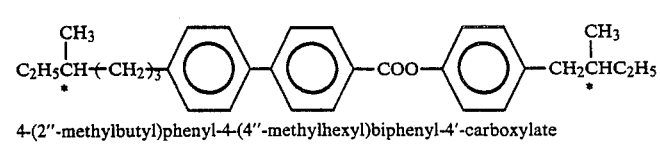

4-(2''-methylbutyl)phenyl-4-(4''-methylhexyl)biphenyl-4'-carboxylate

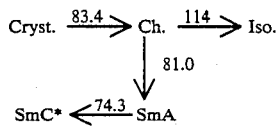

The mesomorphic compound represented by the formula 2-1 may also be mixed with a smectic liquid crystal such as those of the formulas (1)–(5) shown before which per se are not chiral to provide a composition which may be used as a ferroelectric liquid crystal. In this case, the mesomorphic compound represented by the formula 2-1 may preferably be used in an amount of 1–99 wt. %, particularly 5–95 wt. %.

As described above, the optically active compound of the present invention, i.e., 4-alkylbenzenethiol or bis(4-alkylphenyl) disulfide represented by the formula 1-1 or 1-2 is effective in preventing occurrence of reverse domain when added to a nematic liquid crystal.

Further, the 4-alkylbenzenethiol and bis(4-alkylphenyl) disulfide can be bonded to an intermediate for a functional material having appropriate intermolecular force and shape without imparing the optical activity, and therefore susceptible of arbitrary molecular designing.

Further, the addition of at least one species of the 4-alkylbenzenethiol and bis(4-alkylphenyl) disulfide according to the present invention provides a chiral nematic liquid crystal or a chiral smectic liquid crystal having improved performances.

Furthermore, the mesomorphic compound represented by the formula 2-1 according to the present invention shows SmC* phase at a relatively low temperature and stably shows the SmC* phase in a broad temperature range, so that the mesomorphic compound is effectively used as a material for constituting a ferroelectric liquid crystal device. Further, the liquid crystal composition containing at least one species of the mesomorphic compound represented by the formula 2-1 has improved performances through lowering and enlargement in the temperature range for SmC* phase.

The present invention will be explained more specifically with reference to some examples.

EXAMPLE 1-1

Bis(4-(2'-methylbutyl)phenyl) disulfide was produced through the following first to fourth steps.

1st step

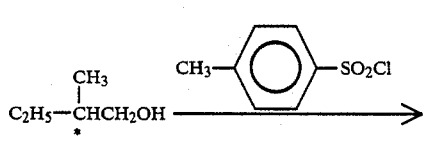

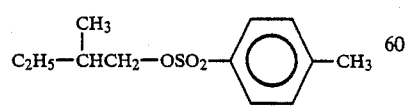

197 g of 2-methylbutyl alcohol (I) was dissolved in 1370 ml of pyridine, and after the solution was cooled to below 10° C. on an ice bath, 512 g of p-toluenesulfonyl chloride was added thereto, followed by 1 hour of stirring. The reaction mixture was left standing overnight in a cool phase and 1500 ml of cold water was added thereto, followed by stirring for 2 hours, extraction with 200 ml of benzene, washing with 5N-HCl and the with water, drying with anhydrous sodium sulfate, and distilling-off of the solvent, whereby 510 g of 2'-methylbutyl 4-methylbenzenesulfonate was obtained.

2nd step

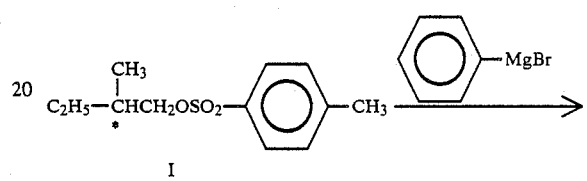

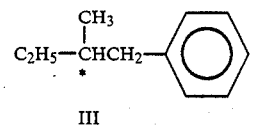

A phenylmagnesium bromide solution prepared from 40 g of bromobenzene, 6.2 g of magnesium and 300 ml of ether was cooled at 5° C., and a mixture liquid of 125 g of 2'-methylbutyl 4-methylbenzenesulfonate (II) prepared above and 130 ml of ether was added dropwise. After 2 hours of stirring, the mixture was elevated in temperature to effect 2 hours of refluxing, followed by standing overnight. To the reaction liquid, 10 % $H_2SO_4$ was added with pH 2. The organic layer was washed successivly with an aqueous sodium bicarbonate solution and water, followed by drying with anhydrous magnesium sulfate, and distilling-off of the solvent. The product was distilled under reduced pressure to obtain 48 g of 4-(2'-methylbutyl)benzene (III), which showed the following IR data:

IR (cm$^{-1}$): 2960, 2940, 2880, 1600, 1500, 1465, 1430, 1380, 1370.

3rd step

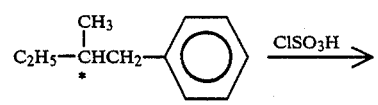

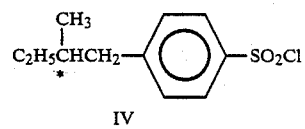

49 g of 4-(2'-methylbutyl)benzene (III) was dissolved in 150 ml of chloroform, and at −10° C., 79 g of ClSO$_3$H was added dropwise in about 1 hour. Thereafter, the mixture was stirred for 6 hours at room temperature. The reaction mixture was then poured on ice and neutralized by an aqueous NaOH solution, followed by distilling-off of the solvent to obtain 380 g of a crystal.

The resultant crystal was dissolved in 350 ml of benzene, and 70 g of PCl5 was added thereto little by little at room temperature. Then, the mixture was stirred for 5 hours at 55° C. and poured on ice. The organic layer was washed with water and separated, followed by drying with anhydrous sodium sulfate and distilling-off of the solvent to obtain an oily product. The oily product was purified by silica gel column chromatography using n-hexane/isopropyl ether as the eluent or migrating phase, thereby to obtain 51 g of 4-(2″-methylbutyl)-benzene-4′-thionylchloride (IV), which showed the IR and NMR data as follows:

IR (cm$^{-1}$): 2980, 2940, 2880, 1600, 1385, 1180.
NMR (ppm): 8.2–7.2 (4H), 2.7–2.5 (2H), 1.6–0.8 (9H).

4th step

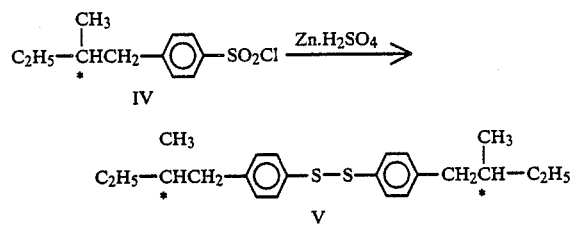

137 g of conc. H2SO4 was dissolved in 410 g of water and cooled to −15° C., and 46.3 g of 4-(2″-methylbutyl)benzene-4′-thionyl chloride (IV) was added thereto dropwise in 20 minutes. After that, 108 g of zinc powder was added below 0° C., and the mixture was stirred for 2.5 hours at −3° C. After being restored to room temperature, the system was raised in temperature and stirred at 45° C. for 70 minutes.

The reaction mixture was subjected to extraction with isotropyl ether, and the extract solution was washed with water and dried with anhydrous sodium sulfate, followed by distilling-off of the solvent to obtain 25 g of an oily product. The oily product was purified by silica gel column chromatography using a 100:1-mixture of n-hexane/ethyl acetate as the eluent, thereby to obtain 1.2 g of bis(4-(2′-methylbutyl)-phenyl) disulfide (V) and 17.0 g of 1:1 mixture of (V) and 4-(2′-methylbutyl)benzenethiol (VI). The NMR data of the product (V) are shown below:

NMR (ppm):
7.4–6.9 (8H), 2.6–2.3 (4H), 1.7–0.8 (18H).

EXAMPLE 1-2

4-(2′-methylbutyl)benzenethiol (V) was prepared through a reduction step involving a reaction represented by the following scheme:

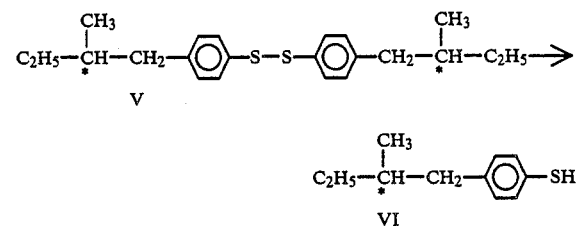

68 g of conc. H2SO4 was poured on 210 g of ice and the mixture was cooled to −12° C. To the mixture, the product mixture obtained in the above Example 1-1 including 1.0 g of (V) and 17 g of the mixture of (V) and (VI) was added dropwise in 40 minutes. Thereafter, 53.6 g of zinc powder was added below 0° C., and the mixture was stirred at −1° C. for 2 hours. After being returned to room temperature, the mixture was gradually raised in temperature and stirred at 59° C. for 2.5 hours. The product showed the following optical rotation, IR and NMR data:

Optical rotation: $[\alpha]_D^{29} = +13.2°$
IR (cm$^{-1}$): 2970, 2930, 2880, 2580, 1600, 1500, 1465, 1150, 1085.
NMR (ppm): 7.2–6.9 (4H), 3.3 (1H), 2.5–2.3 (2H), 1.7–0.8 (9H).

EXAMPLE 1-3

A twisted nematic (TN) cell prepared by using a liquid crystal mixture comprising 1 wt. part of (+)-4-(2′-methylbutyl)benzenethiol of the above Example 1-3 and 99 wt. parts of Lixon GR-63 (biphenyl liquid crystal mixture produced by Chisso K.K.) was observed to provide a nematic phase with remarkably reduced reverse domain as compared with a TN cell prepared without addition of the thiol.

EXAMPLE 1-4

A TN cell prepared by using a liquid crystal mixture comprising 1 wt. part of (+)-bis(4-(2′-methylbutyl)phenyl) disulfide of the above Example 1-1 and 99 wt. parts of Lixon GR 63 was observed to provide a nematic phase with remarkably reduced reverse domain as compared with a TN cell prepared without addition of the disulfide.

EXAMPLE 2-1

S-4′-(2-methylbutyl)phenyl 4-octyloxythiobenzoate represented by the following formula was prepared:

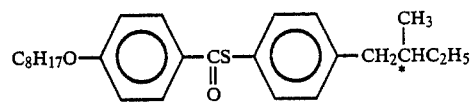

2.78 g of 4-octyloxybenzoic acid was added to 10 ml of benzene, and under stirring at room temperature, 2.36 g of PCl5 was added little by little. The mixture was then heated under reflux for 4 hours. Thereafter, the solvent was distilled off to obtain 4-octyloxybenzoic acid chloride.

2.0 g of 4-(2′-methylbutyl)benzenethiol and 0.88 g of pyridine were dissolved in 10 ml of toluene and the mixture was cooled with ice, to which the 4-octyloxybenzoic acid chloride dissolved in 10 ml of toluene was added in 11 minutes at 2° C. Thereafter, the mixture was stirred at room temperature for 24 hours.

After the reaction, the reaction mixture was poured into cold water and acidified with 6N-HCl to form a precipitate, which was then removed by filtration. The remaining organic layer was washed successively with water, 2N-NaOH aqueous solution and water, and dried with anhydrous sodium sulfate, followed by distilling-off of the solvent to obtain 4.0 g of a crystal.

The above crystal was purified by silica gel column chromatography using a 2/1-mixture liquid of n-hexane/chloroform as the eluent, and then recrystallized from ethanol to obtain 1.17 g of S-4′-(2-methylbutyl)-phenyl 4-octyloxythiobenzoate, which showed the following IR and NMR data:

IR (cm$^{-1}$): 2970, 2925, 2860, 1665, 1605, 1512, 1310, 1270, 1215, 1170, 905.

NMR (ppm): 8.0–6.9 (8H), 4.1–3.9 (2H), 2.6–2.4 (2H), 1.8–0.8 (24H).

EXAMPLES 2-2, 2-4, 2-7, 2-8

Mesomorphic compounds according to the present invention were prepared in similar manner as in Example 2-1. The products are listed in the above mentioned Table 1 together with the phase transition temperatures thereof.

EXAMPLE 2-3

S-4-(2'-methylbutyl)phenyl 4'-heptylbiphenylthiocarboxylate represented by the following formula was prepared:

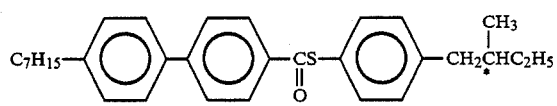

3.29 g of 4-heptylbiphenylcarboxylic acid was added to 10 ml of benzene, and 2.36 g of $PCl_5$ was added little by little under stirring at room temperature, followed by 4 hours of heat-refluxing. Thereafter, the solvent was distilled off to obtain 4-heptylbiphenylcarboxylic acid chloride.

2.0 g of 4-(2'-methylbutyl)benzenethiol and 0.88 g of pyridine were dissolved in 10 ml of toluene, and at 0° C., a solution of the above heptylbiphenylcarboxilic acid chloride in 10 ml of toluene was added dropwise in 15 minutes. Thereafter, the mixture was stirred at room temperature for 24 hours.

After the reaction, the reaction mixture was poured in ice water and acidified with 6N-HCl to result in a precipitate, which was then separated by filtration. The remaining organic layer was successively washed with water, 2N-NaOH aqueous solution and water and dried with anhydrous sodium sulfate, followed by distilling-off of the solvent to obtain 5.0 g of a crude crystal. The crystal was recrystallized from ethanol to obtain 1.7 g of S-4-(2'-methylbutyl)phenyl 4'-heptylbiphenylthiocarboxylate, which showed the following IR and NMR data:

IR ($cm^{-1}$): 2960, 2930, 2855, 1670, 1600, 1495, 1465, 1400, 1175, 912, 810.

NMR (ppm): 8.1–7.1 (12H), 2.8–2.4 (4H), 1.9–0.8 (22H).

EXAMPLE 2-5

A liquid crystal composition was prepared by mixing a known ferroelectric liquid crystal compound 4-(4"-methylhexyloxy)benzoic acid-4'-octyloxyphenyl ester (shown below as "A") and 4-dodecyloxythiobenzoic acid-S-4'-(2-methylbutyl)phenyl ester (shown below as "B") prepared in Example 2-2 in equal amounts as shown below. The resultant liquid crystal composition showed SmC* phase from 53° C. to 16° C. in the course of temperature decrease.

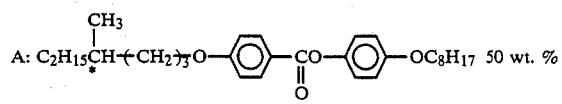

EXAMPLE 2-6

A liquid crystal device was prepared by using the liquid crystal composition prepared in Example 2-5.

More specifically, a 1000 Å-thick ITO film was applied as electrodes onto a highly polished glass substrate of 10×20 mm in size, and an about 1000 Å-thick $SiO_2$ layer was deposited thereon by the ion beam process. On one of the thus tread pair of glass substrates, the liquid crystal composition of Example 2-5 was dropped, and the other substrate was superposed thereon. The substrates were held at 60° C. and mutually slided in a parallel movement while maintaining a spacing therebetween at 1.4 μm and observing them through a polarizing microscope, whereby a homogenously aligned monodomain having lost spiral structure was observed to be formed. In this state, pulses of ±20 volts and 1 msec were applied at 35° C., whereby switching was effected.

What is claimed is:

1. An optically active compound represented by the formula:

$$R_3\!\!-\!\!\left(\!\!\bigcirc\!\!\right)_{\!\!n}\!\!-\!\!\underset{\underset{O}{\parallel}}{C}\!\!-\!\!S\!\!-\!\!\left(\!\!\bigcirc\!\!\right)\!\!-\!\!CH_2\overset{*}{C}HC_2H_5, \qquad 2\text{-}1$$

wherein $R_3$ is an alkyl or alkoxy group having 4–16 carbon atoms, n is 1 or 2, and C* is an asymmetric carbon atom.

2. An optically active compound according to claim 1, which is represented by the formula:

$$C_8H_{17}O\!\!-\!\!\left(\!\!\bigcirc\!\!\right)\!\!-\!\!\underset{\underset{O}{\parallel}}{C}\!\!-\!\!S\!\!-\!\!\left(\!\!\bigcirc\!\!\right)\!\!-\!\!CH_2\overset{*}{C}HC_2H_5.$$

3. An optically active compound according to claim 1, which is represented by the formula:

$$C_{12}H_{25}O\!\!-\!\!\left(\!\!\bigcirc\!\!\right)\!\!-\!\!\underset{\underset{O}{\parallel}}{C}\!\!-\!\!S\!\!-\!\!\left(\!\!\bigcirc\!\!\right)\!\!-\!\!CH_2\overset{*}{C}HC_2H_5.$$

4. An optically active compound according to claim 1, which is represented by the formula:

$$C_7H_{15}O\!\!-\!\!\left(\!\!\bigcirc\!\!\right)\!\!-\!\!\left(\!\!\bigcirc\!\!\right)\!\!-\!\!\underset{\underset{O}{\parallel}}{C}\!\!-\!\!S\!\!-\!\!\left(\!\!\bigcirc\!\!\right)\!\!-\!\!CH_2\overset{*}{C}HC_2H_5.$$

5. An optically active compound according to claim 1, which is represented by the formula:

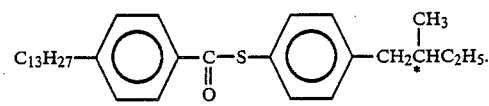

6. An optically active compound according to claim 1, which is represented by the formula:

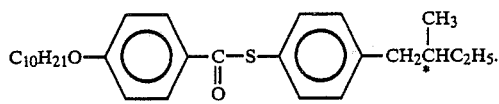

7. An optically active compound according to claim 1, which is represented by the formula:

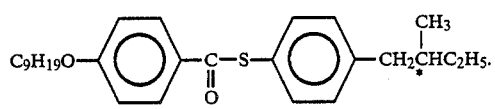

8. A chiral smectic liquid crystal composition comprising at least two components, at least one of which is an optically active compound represented by the formula:

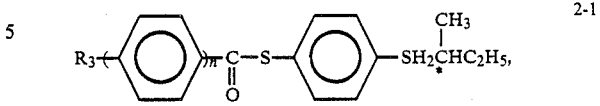

wherein $R_3$ is an alkyl or alkoxy group having 4–16 carbon atoms, n is 1 or 2, and C* is an asymmetric carbon atom.

9. A composition according to claim 8, which contains 1–99 wt. % of the optically active compound in addition to a ferroelectric liquid crystal.

10. A composition according to claim 8, which contains 5–95 wt. % of the optically active compound in addition to a ferroelectric liquid crystal.

11. A composition according to claim 8, which contains 1–99 wt. % of the optically active compound in addition to a smectic liquid crystal.

12. A composition according to claim 8, which contains 5–95 wt. % of the optically active compound in addition to a smectic liquid crystal.

13. A liquid crystal device, comprising a pair of oppositely spaced substrates each having thereon an electrode, and a liquid crystal composition according to claim 8 disposed between the substrates.

* * * * *

UNITED STATES PATENT AND TRADEMARK OFFICE
CERTIFICATE OF CORRECTION

PATENT NO. : 4,816,178
DATED : March 28, 1989
INVENTOR(S) : KAZUHARU KATAGIRI, ET AL.      Page 1 of 2

It is certified that error appears in the above-identified patent and that said Letters Patent is hereby corrected as shown below:

COLUMN 6

Formula (2), "$-\underset{O}{N=N}-$" should read -- $-\underset{\widetilde{O}}{N=N}-$ --.

Formula (4), "$C_8H_{17}O-$" should read --$C_8H_{17}-$ --.

COLUMN 18

Line 63, "$C_7H_{15}O-$" should read --$C_7H_{15}-$ --.

UNITED STATES PATENT AND TRADEMARK OFFICE
CERTIFICATE OF CORRECTION

PATENT NO. : 4,816,178
DATED : March 28, 1989
INVENTOR(S) : KAZUHARU KATAGIRI, ET AL.

It is certified that error appears in the above-identified patent and that said Letters Patent is hereby corrected as shown below:

COLUMN 20

Lines 4-5, " $\begin{array}{c} CH_3 \\ | \\ SH_2\overset{*}{C}HC_2H_5, \end{array}$ "

should read -- $\begin{array}{c} CH_3 \\ | \\ CH_2\overset{*}{C}HC_2H_5, \end{array}$ --.

Signed and Sealed this

Sixth Day of March, 1990

Attest:

JEFFREY M. SAMUELS

Attesting Officer

Acting Commissioner of Patents and Trademarks